United States Patent [19]

Kikumoto et al.

[11] 4,060,612

[45] Nov. 29, 1977

[54] PHARMACEUTICALLY ACTIVE 2-OMEGA-AMINOALKOXYDIPHENYL SULFIDES

[75] Inventors: Ryoji Kikumoto, Machida; Akihiro Tobe, Kawasaki; Shinji Tonomura, Tokyo; Hidenobu Ikoma, Kawasaki, all of Japan

[73] Assignee: Mitsubishi Chemical Industries Ltd., Tokyo, Japan

[21] Appl. No.: 704,493

[22] Filed: July 12, 1976

Related U.S. Application Data

[63] Continuation-in-part of Ser. No. 627,059, Oct. 30, 1975, abandoned.

[51] Int. Cl.$^2$ .................. A01N 9/22; A01N 9/24; C07C 93/06

[52] U.S. Cl. .................. 424/248.52; 260/268 R; 260/501.18; 260/501.19; 260/570.7; 260/294.8 G; 424/267; 424/250; 424/316; 424/330; 544/158

[58] Field of Search ............. 260/247.1, 570.7, 501.18, 260/501.19; 424/248, 316, 330

[56] References Cited

PUBLICATIONS

Toyoshima et al. (I) "Chemical Abstracts", vol. 72, p. 282 Section 3152y (1970).
Toyoshima et al. (II), "J. Pharm. Soc. Japan," vol. 89, pp. 1417–1425 (1970).
Protiva et al., "Chemical Abstracts", vol. 45, p. 577 (1951).

*Primary Examiner*—Robert V. Hines
*Attorney, Agent, or Firm*—Oblon, Fisher, Spivak, McClelland & Maier

[57] ABSTRACT

2-Omega-aminoalkoxydiphenyl sulfides are prepared and found useful as pharmaceutical agents, particularly as antidepressants.

12 Claims, No Drawings

PHARMACEUTICALLY ACTIVE 2-OMEGA-AMINOALKOXYDIPHENYL SULFIDES

CROSS-REFERENCE TO RELATED APPLICATIONS

This application is a continuation-in-part of U.S. application Ser. No. 627,059, filed Oct. 30, 1975 and now abandoned.

BACKGROUND OF THE INVENTION

This invention relates to 2-omega-aminoalkoxydiphenyl sufides and derivatives thereof which are pharmacologically active as antidepressants.

DESCRIPTION OF THE PRIOR ART

Certain 2-omega-aminoalkoxydiphenyl-ether and sulfide compounds have been disclosed, for example, by Protiva et al, CA 45, 577a (1951); and Toyoshima et al, J. Pharm. Soc. Jap. 89, 1417–1425 (1970). However, these compounds are not fully satisfactory in their pharmacological activity, especially as antidepressants.

SUMMARY OF THE INVENTION

Accordingly, it is an object of the present invention to provide new compounds which are pharmaceutically active, particularly as antidepressants.

Briefly, this and other objects of this invention as will hereinafter become clear from the ensuing discussion have been attained by providing compounds of the formula:

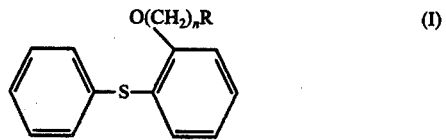

wherein $n$ is 3–5 and when $n = 3$, R is $C_1$–$C_5$ alkylamino; when $n = 4$, R is amino, $C_1$–$C_5$ alkylamino, $C_2$–$C_6$ dialkylamino or morpholino; and when $n = 5$, R is $C_2$–$C_6$ dialkylamino or morpholino, and acid addition salts thereof.

This invention also provides a method for palliating conditions of depression in warm-blooded animals which comprises administering to said animal an antidepressively effective amount of a compound of Formula I, and a method for producing such compounds which comprises reacting an omegahalogenoalkoxyldiphenyl sulfide of the formula:

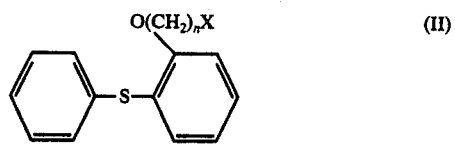

wherein X is a halogen; such as F, Cl, Br or I and $n$ is as defined above, with an amine of the formula:

 R-H   (III)

wherein R is as defined above for each $n$.

DESCRIPTION OF THE PREFERRED EMBODIMENTS

As summarized above, this invention relates to a group of compounds useful as pharmaceutical agents, which compounds are represented by Formula I above.

Illustrative of these compounds are the following:
2-(3-methylaminopropoxy)diphenyl sulfide,
2-(4-aminobutoxy)diphenyl sulfide,
2-(4-methylaminobutoxy)diphenyl sulfide,
2-(4-dimethylaminobutoxy)diphenyl sulfide,
2-(4-morpholinobutoxy)diphenyl sulfide,
2-(5-dimethylaminopentyloxy)diphenyl sulfide.

The pharmaceutically acceptable acid addition salts of the above compounds are of course also included within the scope of this invention. It will be understood that the term "pharmaceutically acceptable acid addition salts" as used herein is intended to include non-toxic salts of the compounds of this invention with an anion. Representative of such salts are hydrochlorides, hydrobromides, sulfates, phosphates, nitrates, acetates, adipates, propionates, tartrates, maleates, citrates, benzoates, toluenesulfonates, and methanesulfonates and the like.

Of the compounds of this invention, the following compounds are most preferred due to their high level of antidepressant activity and their low level of toxicity:
2-(3-methylaminopropoxy)diphenyl sulfide.
2-(4-methylaminobutoxy)diphenyl sulfide,
2-(4-dimethylaminobutoxy)diphenyl sulfide.

Also very preferred are: 2-(4-aminobutoxy)diphenyl sulfide and 2-(4-morpholinobutoxy)diphenyl sulfide. Also preferred is 2-(5-dimethylaminopentyloxy)diphenyl sulfide.

PREPARATION

The compounds of this invention are prepared by reacting an omegahalogenoalkoxydiphenyl sulfide with an amine. Suitable omega-halogenoalkoxydiphenyl sulfide starting materials which are represented by Formula II above can be prepared by reacting 2-hydroxydiphenyl sulfide with 1,3-dihalogenopropane, 1,4-dihalogenobutane or 1,5-dihalogenopentane in the presence of an alkali. Suitable amine starting materials which are represented by Formula III above include ammonia; primary amines such as methylamine, ethylamine, isopropylamine and the like; secondary amines such as dimethylamine, diethylamine, N-methylethylamine and the like; and morpholine. The amine can be reacted with an equimolar amount of the omegahalogenoalkoxydiphenyl sulfide. However, the use of an excess amine accelerates the reaction. Normally, the amount of the amine to be employed is in the range of 1 to 100 moles per 1 mole of the omega-halogeno-alkoxydiphenyl sulfide. The reaction can be carried out without an added solvent. However, the use of a reaction-inert solvent makes a homogenous reaction possible. Suitable solvents include water, dioxane, tetrahydrofuran, dimethyl sulfoxide, lower aliphatic alcohols and mixtures thereof. The reaction temperature is not critical, but normally ranges from room temperatures to 150° C. The reaction time varies widely with the reaction temperature and the reactivity of the starting materials, but normally is in the range of from 10 minutes to 40 hours. The presence of bases which neutralize the hydrogen halide formed in the course of the reaction also accelerates the reaction. Suitable bases include inorganic bases such as potassium hydroxide, sodium hydroxide, potassium carbonate, sodium carbonate and the like; and tertiary amines such as pyridine, triethylamine and the like. The amount of the base to be employed is normally in the range of from 1 to 5 moles per one mole of the omega-halogenoalkoxydiphenyl sulfide. When the base is absent, the omega-aminoalkoxydiphenyl sulfide reacts with the hydrogen halide formed during the reaction, and is converted to the acid addition salt thereof.

Acid addition salts of the 2-omega-aminoalkoxydiphenyl sulfides may be conveniently prepared by contacting the compounds with a suitable acid. The 2-omega-aminoalkoxydiphenyl sufides and the acid addition salts thereof may be purified by recrystallization employed a suitable solvent such as alcohol-ether.

Pharmacological testing of the 2-omega-aminoalkoxydiphenyl sulfides has demonstrated that they are useful as antidepressant agents, as evidenced by their ability to reverse reserpine hypothermia in mice. Anticonvulsant activity has also been discovered in the compounds of this invention. The compounds have been tested in mice for antidepressant, sedative, anticonvulsant and anticholinergic activity. The compounds were administered intraperitoneally and the activities of the compounds were compared with those of Amitriptyline. Antidepressant activity was evaluated by antagonism of reserpine (5 mg/kg, i.p.) induced hypothermia (P. S. J. Spencer in "Antidepressant Drugs", S. Garattini and M. N. G. Duhes, ed., Excerpta Medica Foundation, Amsterdam, pages 194–204 (1967)) and antireserpine activity was expressed as relative potency (Amitriptyline = 1). $LD_{50}$ was calculated by the Litchfield-Wilcoxon method. CNS depressant activity was defined by the ability of the compounds to cause neurological deficit as measured by a traction test (S. Courvoisier, R. Ducrot, L. Julou; "Psychotropic Drugs" ed. by S. Garattini, V. Ghetti, page 373 (1957)) and spontaneous motor activity. (Spontaneous motor activity was measured by an ANIMEX apparatus.) Anticonvulsant activity was determined by antagonism of electroshock induced tonic extensor [L. S. Goodman, M. Singh Grewal, W. C. Brown and E. A. Swinyard, J. Pharmacol, Exptal. Therap., 108, 168 (1953)]. Central anticholinergic effect was assessed by testing a tremorine induced tremor in mice [G. M. Everett, L. E. Bloucus and J. M. Sheppard, Science 124, 79 (1956)]. Results of these tests are summarized in Tables I and II, in which $ED_{50}$ is defined as the dose of the test compounds which prevents 50% of each response.

TABLE 1

| Compound | m.p. (° C) | Relative Potency | LD50 (mg/kg i.p.) |
|---|---|---|---|
| Amitriptyline | | 1.00 | 65 |
| 2-(2-dimethylaminoethoxy) diphenyl ether hydrochloride [prior art] | 131–132 | 0 | |
| 2-(3-dimethylaminopropoxy) diphenyl ether hydrochloride [prior art] | 139–141.5 | 0.14 | |
| 2-(3-dimethylaminopropoxy) diphenyl sulfide hydrochloride [prior art] | 98–100.5 | 0 | |
| 2-(3-methylaminopropoxy) diphenyl sulfide hydrochloride | 99–102 | 0.60 | 135 |
| 2-(4-aminobutoxy) diphenyl sulfide hydrochloride | 78–81 | 0.36 | |
| 2-(4-methylaminobutoxy) diphenyl sulfide hydrochloride | 143–147 | 0.90 | 120 |
| 2-(4-dimethylaminobutoxy) diphenyl sulfide hydrochloride | 140–146 | 0.70 | 130 |
| 2-(4-morpholinobutoxy) diphenyl sulfide hydrochloride | 106–109 | 0.38 | |
| 2-(5-dimethylaminopentyloxy) diphenyl sulfide hydrochloride | 95–96 | 0.15 | |

The following compounds, none of which form a part of this invention, were also tested for antireserpine activity as were the compunds of Table 1 and all displayed a relative potency of 0: 2-(4-(1-piperidyl)butoxy) diphenyl sulfide hydrochloride (m.p. 126°–128° C); 2-(4-(4-methyl-1-piperazinyl)-butoxy)diphenyl sulfide dihydrochloride (m.p. 180°–187° C); and 2-(5-methylaminopentyloxy) diphenyl sulfide hydrochloride (powder).

Table II

| | CNS Depressant, Anticonvulsant and Central Anticholinergic Activity in Mice | | | |
|---|---|---|---|---|
| Compound | Anticonvulsant Activity ED50 (mg/kg i.p.) | Muscle Relaxant Action ED50 (mg/kg i.p.) | Spontaneous Motor Activity Depression ED50 (mg/kg i.p.) | Antitremorine Effect ED50 (mg/kg i.p.) |
| 2-(4-methylaminobutoxy)-diphenyl sulfide hydrochloride | >60 | 50 | >60 | 30 |
| Amitriptyline | 16 | 15 | 18 | 4 |

It is apparent from Tables I and II that 2-(4-methylaminobutoxy) diphenyl sulfide exhibits antireserpine activity comparable to that of Amitriptyline, while it exhibits low toxicity, weak CNS depressant and anticholinergic action.

The compound of this invention can be administered by any means that effects the palliating of conditions of depression in warm-blooded animals. For example, administration can be parenterally, subcutaneously, intravenously, intramuscularly, or intraperitoneally. Alternatively or concurrently, administration can be orally. The approximate dosage to be administered will be dependent upon the age, health and weight of the recipient, the extent of depression, the kind of concurrent treatment if any, the frequency of treatment, and the nature of the effect desired. Dosage can be determined by conventional considerations. Generally, the daily dosage of active ingredient compound will be from about 0.5 to 50 mg per kg of body weight. Normally, from 1 to 30 mg per kg per day, in one or more applications per day is effective to obtain the desired result.

The compounds of Formula I can be employed in solid dosage froms such as tablets, capsules, powder packets, or in liquid forms such as solutions, suspensions, or elixirs, for oral administration, or in sterile liquid formulations such as solutions or suspensions for parenteral use. In such compositions, the active ingredient will ordinarily be present in an amount of at least 0.5% by weight based on the total weight of the composition and not more than 90% by weight. In addition to the active ingredient of this invention, the compositions can contain a solid or liquid non-toxic pharmaceutical carrier for the active ingredient. In one embodiment of a suitable composition, the solid carrier can be a capsule of the ordinary gelatin type. The capsule can contain from about 30-60% by weight of a compound of Formula I and 70–40% of a carrier. In another embodiment, the active ingredient can be tableted with or without adjuvants, or put into power packets. These capsules, tablets and powders will generally constitute from about 5% to about 95% and preferably from 25% to 90% by weight of active ingredient. In general, these dosage forms preferably contain from about 5 to about 500 mg of active ingredients, with from about 25 to about 250 mg being most preferred. Suitable pharmaceutical carriers include sterile liquids such as water and oils, including those of petroleum, animals, vegetable or synthetic origin, such as peanut oil, soybean oil, mineral oil, and the like. In general, water saline, aqueous dextrose and related sugar solutions, and glycols such as ethylene glycol, propylene glycol and polyethylene glycol are preferred liquid carriers, particularly for injectible solutions. These compositions will ordinarily contain from about 0.5% to 20%, preferably from about 1 to 10%, by weight of the active ingredient. As mentioned above, oral administration can be effected by a suitable suspension or syrup, of which the active ingredient normally will constitute from about 0.5 to 10% by weight. Suitable pharmaceutical carriers in such compositions include watery vehicles such as aromatic waters, syrups or pharmaceutical mucilages.

Having generally described the invention, a more complete understanding can be obtained by reference to certain specific examples, which are provided herein for purposes of illustration only and are not intended to be limiting unless otherwise specified.

EXAMPLE 1

A solution of 5.0 g of 2-(4-bromobutoxy)diphenyl sulfide, 30 ml of 40% dimethylamine aqueous solution, and 100 ml of ethanol was allowed to stand at room temperature for 8 hours. Ethanol and excess dimethylamine were distilled in vacuo, 2N-NaOH aqueous solution was added, and the reaction product was extracted with ether. The ether solution was distilled, 2N-HCl solution was added and the solution was evaporated to dryness. The residue was recrystallized from ethanol -ether yielding 4.6g (91% yield) of 2-(4-dimethylaminobutoxy)-diphenyl sulfide hydrochloride, m.p. 140°–146° C.

Analysis-for $C_{18}H_{23}NOS.HCl$ percent. Calculated-C, 63.98; H, 7.16; N, 4.15. Measured-C, 63.84; H, 7.19; N, 3.96.

EXAMPLE 2

A solution of 5.0 g of 2-(3-bromopropoxy)diphenyl sulfide and 6 g of methylamine in 100 ml of ethanol was heated at a temperature of 50° C for 2 hours in a sealed tube. Ethanol and excess methylamine were distilled in vacuo, 2N-NaOH aqueous solution was added, and the reaction product was extracted with ether. Dry hydrogen chloride gas was passed into the ether solution, and the precipitate was collected by filtration. Recrystallization from ethanol -ether yielded 4.1 g. (86% yield) of 2-(3-methylaminopropoxy) diphenyl sulfide hydrochloride, m.p. 99° – 102° C.

Analysis-for $C_{16}H_{19}NOS.HCl$ (percent). Calculated-C, 62.02; H, 6.51; N, 4.52. Measured-C, 61.84; H, 6.35; N, 4.42.

EXAMPLES 3–6

The commpounds in the following table were prepared according to the procedure described in either Example 1 or 2, using the appropriate starting materials.

Having now fully described the invention, it will be apparent to one of ordinary skill in the art that many changes and modifications can be made thereto without departing from the spirit or scope of the invention as set forth herein.

| Example No. | Formula | Addition Moiety | Preparation Process (Ex. No.) | m.p. (° C) | Analysis Upper: Calcd. Lower: Found | | |
|---|---|---|---|---|---|---|---|
| | | | | | C | H | N |
| 3 | 2-(O—(CH$_2$)$_4$NH$_2$) diphenyl sulfide | HCl | 1 | 78–81 | 62.02 | 6.51 | 4.52 |
| | | | | | 61.98 | 6.50 | 4.39 |
| 4 | 2-(O—(CH$_2$)$_4$N(CH$_3$)H) diphenyl sulfide | HCl | 1 | 143–147 | 63.04 | 6.85 | 4.33 |
| | | | | | 63.15 | 6.87 | 4.26 |
| 5 | 2-(O—(CH$_2$)$_5$N(CH$_3$)$_2$) diphenyl sulfide | HCl | 2 | 95–96 | 64.84 | 7.45 | 3.98 |
| | | | | | 64.81 | 7.45 | 3.89 |
| 6 | 2-(O—(CH$_2$)$_4$-morpholino) diphenyl sulfide | HCl | 1 | 106–109 | 63.22 | 6.90 | 3.69 |
| | | | | | 63.20 | 6.89 | 3.61 |

What is claimed as new and intended to be covered by letters patent is:

1. A 2-omega-aminoalkoxydiphenyl sulfide compound having the formula:

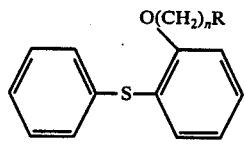

wherein $n$ is 3–5 and when $n = 3$, R is $C_1$–$C_5$ alkylamino; when $n = 4$, R is amino, $C_1$–$C_5$ alkylamino, $C_2$–$C_6$ dialkylamino or morpholino; and when $n = 5$, R is $C_2$–$C_6$ dialkylamino or morpholino, and acid addition salts thereof.

2. The compound of claim 1 wherein R is selected from the group consisting of amino, methylamino, dimethylamino and morpholino.

3. The compound of claim 1 which is 2-(3-methylaminopropoxy)-diphenyl sulfide.

4. The compound of claim 1 which is 2-(4-methylaminobutoxy)-diphenyl sulfide.

5. The compound of claim 1 which is 2-(4-dimethylaminobutoxy)-diphenyl sulfide.

6. The compound of claim 1 which is 2-(4-aminobutoxy) diphenyl sulfide.

7. The compound of claim 1 which is 2-(4-morpholinobutoxy)-diphenyl sulfide.

8. The compound of claim 1 which is 2-(5-dimethylaminopentyloxy)-diphenyl sulfide.

9. A compound of claim 1 selected from the group consisting of 2-(3-methylaminopropoxy)-diphenyl sulfide, 2-(4-methylaminobutoxy)-diphenyl sulfide and 2-(4-dimethylaminobutoxy)-diphenyl sulfide.

10. A compound of claim 1 selected from the group consisting of 2-(3-methylaminopropoxy)-diphenyl sulfide, 2-(4-methylaminobutoxy)-diphenyl sulfide, 2-(4-dimethylaminobutoxy)-diphenyl sulfide, 2-(4-aminobutoxy) diphenyl sulfide and 2-(4-morpholinobutoxy)-diphenyl sulfide.

11. The compound of claim 1 wherein R is amino, $C_1$–$C_5$ alkylamino or $C_2$–$C_6$ dialkylamino.

12. An antidepressant composition which comprises an antidepressant effective amount of a compound of claim 1 and a pharmaceutically acceptable adjuvant.

* * * * *